United States Patent
Barbarat et al.

(10) Patent No.: US 11,229,806 B2
(45) Date of Patent: Jan. 25, 2022

(54) COLD ATMOSPHERIC PLASMA TREATMENT WITH CHEMICAL OR ORGANIC COMPOUNDS TO MODIFY THE KERATINOUS SUBSTRATE MICROBIOTA

(71) Applicant: L'OREAL, Paris (FR)

(72) Inventors: Philippe Barbarat, Colombes (FR); Richard Martin, Rochecorbon (FR); Matthieu Jacob, Paris (FR)

(73) Assignee: L'OREAL, Paris (FR)

( * ) Notice: Subject to any disclaimer, the term of this patent is extended or adjusted under 35 U.S.C. 154(b) by 474 days.

(21) Appl. No.: 15/973,931

(22) Filed: May 8, 2018

(65) Prior Publication Data
US 2018/0318596 A1 Nov. 8, 2018

Related U.S. Application Data

(60) Provisional application No. 62/502,950, filed on May 8, 2017.

(51) Int. Cl.
*A61N 1/44* (2006.01)
*A61K 35/741* (2015.01)
(Continued)

(52) U.S. Cl.
CPC .............. *A61N 1/44* (2013.01); *A61K 35/741* (2013.01); *A61K 35/744* (2013.01);
(Continued)

(58) Field of Classification Search
CPC ...... A61N 1/44; A61K 35/741; A61K 35/744; A61K 35/745; A61K 35/747; A61L 2/0011; A61L 2/14; A61M 37/00; H05H 1/2406
(Continued)

(56) References Cited

U.S. PATENT DOCUMENTS

| | | | |
|---|---|---|---|
| 2011/0014248 A1* | 1/2011 | Castiel | A61K 8/0229 424/401 |
| 2012/0046602 A1 | 2/2012 | Morfill et al. | |
| 2013/0068226 A1* | 3/2013 | Watson | H05H 1/2406 128/203.29 |

(Continued)

FOREIGN PATENT DOCUMENTS

| | | |
|---|---|---|
| CN | 102131495 A | 7/2011 |
| CN | 105339048 A | 2/2016 |

(Continued)

OTHER PUBLICATIONS

Hoffmann C, Berganza C, Zhang J. Cold Atmospheric Plasma: methods of production and application in dentistry and oncology. Med Gas Res. 2013;3(1):21. Published Oct. 1, 2013. doi:10.1186/2045-9912-3-21 (Year: 2013).*

(Continued)

*Primary Examiner* — Andrew J Mensh
(74) *Attorney, Agent, or Firm* — Oblon, McClelland, Maier & Neustadt, L.L.P.

(57) ABSTRACT

A skin microbiota modulation device that includes a cold plasma assembly configured to generate a cold plasma stimulus including a partially ionized gas mixture and to interrogate a biological surface with the cold plasma stimulus; and a microbiota seeding assembly including one or more target species of micobiota, the microbiota seeding assembly configured to deliver the one or more target species of micobiota to the biological surface.

18 Claims, 16 Drawing Sheets

(51) Int. Cl.
| | |
|---|---|
| *A61M 37/00* | (2006.01) |
| *A61K 35/747* | (2015.01) |
| *A61K 35/744* | (2015.01) |
| *A61K 35/745* | (2015.01) |
| *A61L 2/14* | (2006.01) |
| *H05H 1/24* | (2006.01) |
| *A61L 2/00* | (2006.01) |
| *A61K 35/00* | (2006.01) |
| *A61B 18/04* | (2006.01) |
| *A61M 35/00* | (2006.01) |

(52) U.S. Cl.
CPC .......... *A61K 35/745* (2013.01); *A61K 35/747* (2013.01); *A61L 2/0011* (2013.01); *A61L 2/14* (2013.01); *A61M 37/00* (2013.01); *H05H 1/2406* (2013.01); *A61B 18/042* (2013.01); *A61K 2035/115* (2013.01); *A61L 2/0047* (2013.01); *A61L 2/0052* (2013.01); *A61L 2/0058* (2013.01); *A61L 2202/11* (2013.01); *A61M 35/00* (2013.01); *A61M 2037/0007* (2013.01)

(58) Field of Classification Search
USPC ........................................................ 604/289
See application file for complete search history.

(56) References Cited

U.S. PATENT DOCUMENTS

2014/0207053 A1* 7/2014 Morfill .................. A61L 2/0011
 604/24
2015/0094647 A1* 4/2015 Kalghatgi ............ A61B 18/042
 604/23
2016/0136062 A1* 5/2016 Woodland ................ A61K 8/19
 424/600
2017/0000167 A1 1/2017 Corrigan

FOREIGN PATENT DOCUMENTS

| EP | 2 170 022 A1 | 3/2010 |
|---|---|---|
| KR | 10-2004-0096576 A | 11/2004 |
| KR | 10-2016-0082680 A | 7/2016 |
| WO | WO 2012/106735 A2 | 8/2012 |
| WO | WO 2012/106735 A3 | 8/2012 |
| WO | WO 2015/039137 A1 | 3/2015 |

OTHER PUBLICATIONS

International Search Report and Written Opinion dated Jul. 25, 2018 in PCT/IB2018/000588, 17 pages.
European Office Action dated Oct. 30, 2019 in Patent Application No. 18734286.0, 3 pages.
European Office Action dated Mar. 12, 2021 in European Patent Application No. 18734286.0, 5 pages.
Office Action dated Apr. 14, 2021, in Korean Patent Application No. 10-2019-7030683 (with English-language translation).
Office Action dated Oct. 28, 2021, in Korean Patent Application No. 10-2019-7030683 (with English-language translation).
Office Action dated Aug. 24, 2021, in Chinese Patent Application No. 201880029686.3 (No available English translation), 10 Pages.

* cited by examiner

| Species (origin) | Associated disorder | Culture conditions |
|---|---|---|
| Staphylococcus aureus (wild & collection) | Atopy | 24h of incubation at 35°C on Trypcase soybean agar (TSA) |
| Corynebacterium xerosis (collection) | Axillary odor | 24h of incubation at 35°C on TSA |
| Corynebacterium jeikeium (collection) | Axillary odor | 24h of incubation at 35°C on TSA + Tween 80 at 1% |
| Staphylococcus haemolyticus (wild & collection) | Axillary odor | 24h of incubation at 35°C on TSA |
| Propionibacterium acnes (wild & collection) | Acne/imperfections | 3 days of incubation at 35°C on TSA in anaerobic conditions |

Fig. 4A

| Species (origin) | Associated disorder | Culture conditions |
|---|---|---|
| *Malassezia furfur* (collection) | Dandruff | 3 days of incubation at 35°C on Sabouraud agar + olive oil at 2.5% |
| *Staphylococcus epidermidis* (wild & collection) | none (Saprophytic strain) | 24h of incubation at 35°C on TSA |
| *Pseudomonas aeruginosa* (wild & collection) | folliculitis (pathogen) | 24h of incubation at 35°C on TSA |
| *Escherichia coli* (wild & collection) | urinary tract infection (pathogen) | 24h of incubation at 35°C on TSA |
| *Candida albicans* (collection) | mycosis (pathogen) | 24h of incubation at 35°C on Sabouraud agar |

Fig. 4B

| Species (origin) | Time T0: 0h immediate 1 3min | Efficacy (characterized) | Ranking (problematic) |
|---|---|---|---|
| Staphylococcus aureus (wild) | | Strong at 3 min (time effect) | 2 (atopy) |
| Staphylococcus aureus (collection) | | Strong at 3 min (time effect) | 2 (atopy) |
| Corynebacterium xerosis (collection) | | Average at 3 min (time effect) | 13 (axillary odor) |
| Corynebacterium jeikeium (collection) | | Average at 3 min (time effect) | 13 (axillary odor) |
| Staphylococcus haemolyticus (wild) | | Strong at 3 min (time effect) | 2 (axillary odor) |
| Staphylococcus haemolyticus (collection) | | Average at 3 min (time effect) | 13 (axillary odor) |

Fig. 6A

| | | | |
|---|---|---|---|
| *Propionibacterium acnes (wild)* | | Strong at 3 min (time effect) | 2 (acne) |
| *Propionibacterium acnes (collection)* | | Strong at 3 min (time effect) | 2 (acne) |
| *Malassezia furfur (collection)* | | Low at 3 min (time effect) | 16 (dandruff) |
| *Staphylococcus epidermidis (wild)* | | Strong at 3 min (time effect) | 2 (Saprophytic strain) |
| *Staphylococcus epidermidis (collection)* | | Strong from 1 min 30s (time effect) | 1 (Saprophytic strain) |
| *Pseudomonas aeruginosa (wild)* | | Strong at 3 min (time effect) | 2 (Pathogen) |
| *Pseudomonas aeruginosa (collection)* | | Strong at 3 min (time effect) | 2 (Pathogen) |

Fig. 6B

| Escherichia coli (wild) | | Strong at 3 min (time effect) | 2 (Pathogen) |
| Escherichia coli (collection) | | Strong from 3 min (time effect) | 4 (Pathogen) |
| Candida albicans (collection) | | Average from 1 min 30s (time effect) | 12 (Pathogen) |

Fig. 6C

| Species (origin) | Time | | | Efficacy (characteristics) | Ranking (problematic) |
|---|---|---|---|---|---|
| | 1m | 1min 30s | 3min | | |
| Staphylococcus aureus (wild) | | | | Low at 3 min (time effect) | 10 (Atopy) |
| Staphylococcus aureus (collection) | | | | Low at 3 min (time effect) | 10 (Atopy) |
| Corynebacterium xerosis (collection) | | | | Average at 3 min (time effect) | 5 (axillary odor) |
| Corynebacterium jeikeium (collection) | | | | Average at 3 min (time effect) | 5 (axillary odor) |
| Staphylococcus haemolyticus (wild) | | | | Low at 3 min (time effect) | 10 (axillary odor) |
| Staphylococcus haemolyticus (collection) | | | | Low at 3 min (time effect) | 10 (axillary odor) |
| Propionibacterium acnes (wild) | | | | Strong from 1 min 30s (time effect) | 1 (acne) |
| Propionibacterium acnes (collection) | | | | Strong at 3 min (time effect) | 2 (acne) |
| Malassezia furfur (collection) | | | | No effect to 3 min | 16 (dandruff) |
| Staphylococcus epidermidis (sauvage) | | | | Low at any time | 7 (Saprophytic strain) |
| Staphylococcus epidermidis (collection) | | | | Average from 1min30 | 4 (Saprophytic strain) |
| Pseudomonas aeruginosa (sauvage) | | | | Low at 3 min (time effect) | 10 (Pathogen) |

Fig. 7A

| | | | |
|---|---|---|---|
| Pseudomonas aeruginosa (collection) | No effect to 3 min (partial inhibition) | 15 (Pathogen) | |
| Escherichia coli (wild) | Low at 1min30 | 9 (Pathogen) | |
| Escherichia coli (collection) | Low at any time | 7 (Pathogen) | |
| Candida albicans (collection) | Strong at 3 min | 2 (Pathogen) | |

Fig. 7B

| | | | |
|---|---|---|---|
| Corynebacterium xerosis (collection) | | Strong from 1 min 30s | 3 (axillary odor) |
| Corynebacterium jeikeium (collection) | | Strong from 1 min 30s | 3 (axillary odor) |
| Staphylococcus haemolyticus (wild) | | Strong from 1 min 30s | 3 (axillary odor) |
| Staphylococcus haemolyticus (collection) | | Average at 2 min 30s | 14 (axillary odor) |
| Propionibacterium acnes (wild) | | Strong from 1 min 30s | 3 (acne) |
| Propionibacterium acnes (collection) | | Strong from 1 min 30s | 3 (acne) |
| Malassezia furfur (collection) | | Strong at 2 min 30s | 9 (dandruff) |
| Staphylococcus epidermidis (wild) | | Strong from 1 min 30s | 3 (Saprophytic strain) |
| Staphylococcus epidermidis (collection) | | Strong from 30s | 1 (Saprophytic strain) |
| Pseudomonas aeruginosa (wild) | | Average at 2 min 30s | 14 (pathogen) |
| Pseudomonas aeruginosa (collection) | | Strong from 1 min 30s | 3 (Pathogen) |

Fig. 8B

| Escherichia coli (wild) | Strong at 2 min 30s | 10 (Pathogen) |
| Escherichia coli (collection) | Strong at 2 min 30s | 10 (Pathogen) |
| Candida albicans (collection) | Strong from 30s | 1 (Pathogen) |

Fig. 8C

COLD ATMOSPHERIC PLASMA TREATMENT WITH CHEMICAL OR ORGANIC COMPOUNDS TO MODIFY THE KERATINOUS SUBSTRATE MICROBIOTA

CROSS-REFERENCE TO RELATED APPLICATIONS

This application claims the benefit of priority from U.S. Provisional Application No. 62/502,950 filed May 8, 2017, the entire contents of which are incorporated herein by reference.

BACKGROUND

Cold Atmospheric Plasma (CAP) technology, also known as non-thermal or non-equilibrium plasma, can be used for its antimicrobial effect. This technology finds utility in medical applications (such as treatment of different kind of skin diseases) and is and considered effective in inactivation of various parasites and foreign organisms.

The generic capability of CAPs against microorganisms has been established under controlled laboratory conditions. CAPs have been shown, by many different groups, to be very effective against gram-negative bacteria, gram-positive bacteria, spores, biofilm-forming bacteria, virus and fungi [see Plasma medicine: an introductory review, M G Kong, New Journal of Physics 11 (2009) 115012 (35pp)].

SUMMARY

The present applicants have recognized that chemical or organic compounds can act beneficially on the microbial environment of the skin or keratinous substrate. For example prebiotics and probiotics may selectively act on skin microbiota. They can inhibit detrimental organisms and at the same time preserve and/or promote beneficial bacteria.

In an aspect, the present disclosure is directed to, among other things, technologies and methodologies that associate both cold atmospheric plasma treatment and treatments with chemical or organic compounds such as pre/pro or post biotic to positively act on the modification of a keratinous substrate microbiota (for example skin microbiota) and fight skin disorders such as atopy, psoriasis, acne, body odor, greasy skin, rosacea, dry skin, pollution and dandruff.

In an aspect, the present disclosure is directed to, among other things, methods and systems which associate both cold atmospheric plasma treatments and chemical or organic compounds treatments (for example pre/pro/post biotic) to modify a keratinous to substrate microbiota (for example: skin, scalp or hair) and help to fight skin disorders such as atopy, psoriasis, acne, body odor, greasy skin, rosacea, dry skin, pollution and dandruff.

One possible treatment association is to first treat a keratinous substrate area with cold atmospheric plasma as a pre-treatment before applying a topical chemical or organic compounds treatment (for example pre/pro or post biotic).

The opposite can also be envisaged: cold atmospheric plasma treatment can be applied as a post-treatment after a topical chemical or organic compounds treatment (for example pre/pro or post biotic). Cold atmospheric plasma (CAP) used as a pretreatment is able to decrease global bacterial concentration and/or balance, and in the same time the pretreatment with pre/pro or post biotic, including chemicals and/or organic compounds help the promotion of chosen microorganisms naturally present on the skin (endogenous bacteria). After CAP treatment, and depending of the growth rate of each OTU (Operational Taxonomic Unit—mean bacterium specie) we can easily understand that the bacterial picture evolve during hours after exposition. Addition of pre/pro post biotic will have different effects on the global bacterial landscape. For example, Gram negative bacteria are more fragile than Gram positive ones, and CAP, providing energy, impact Gram+/Gram− balance.

A simultaneous treatment of cold atmospheric plasma and chemical or organic compounds can also be envisaged.

In an embodiment, a skin microbiota modulation device is provided, comprising: a cold plasma assembly configured to generate a cold plasma stimulus including a partially ionized gas mixture and to interrogate a biological surface with the cold plasma stimulus; and a microbiota seeding assembly including one or more target species of microbiota, the microbiota seeding assembly configured to deliver the one or more target species of microbiota to the biological surface.

In an embodiment, the cold plasma assembly is configured to generate a cold plasma stimulus having one or more of electrically charged particles, electrically uncharged particles, electrons, ions, molecules, and the like.

In an embodiment, the cold plasma assembly is configured to generate a cold plasma stimulus having one or more of Ultraviolet(UV) radiation, visible (VIS) radiation, Infrared (IR) radiation, and the like.

In an embodiment, the cold plasma assembly is configured to generate a cold plasma stimulus having one or more of Argon, Heliox, Helium, Nitrogen, Oxygen, and the like.

In an embodiment, the cold plasma assembly is configured to deliver to a biological surface one or more of Ultraviolet(UV) radiation, visible (VIS) radiation, Infrared (IR) radiation, free radicals, electrically charged particles, electrically uncharged particles, electrons, ions, molecules, a gas stream, and the like.

In an embodiment, the cold plasma assembly includes at least one of an atmospheric pressure plasma jet, a dielectric barrier discharge plasma actuator, a gliding arc device, a piezoelectric direct discharge plasma device, a plasma actuator, a plasma needle, a plasma pencil, and the like.

In an embodiment, the cold plasma assembly is configured to generate a cold plasma stimulus of a character and for a duration sufficient to modulate the activity of skin microbiota on the biological surface.

In an embodiment, the cold plasma assembly is configured to deliver a cold plasma stimulus for a duration sufficient to modulate the activity of skin microbiota on the biological surface without damaging tissue.

In an embodiment, the cold plasma assembly is configured to generate a cold plasma stimulus that is less than 40° Celsius at the point of application. In an embodiment, the cold plasma assembly is configured to generate a cold plasma stimulus having a temperature ranging from about 26° Celsius to about 60° Celsius at the point of application. In an embodiment, the cold plasma assembly is configured to generate a cold plasma stimulus having a temperature ranging from about 30° Celsius to about 50° Celsius at the point of application. In an embodiment, the temperature of the cold plasma stimulus at the point of application is in part determined by the duration, intensity, frequency, heat transfer coefficient, and the like associated with the cold plasma stimulus.

In an embodiment, the degree of ionization of a plasma ($\alpha$) comprises the proportion of charged particles to the total number of particles including neutrals and ions. In an embodiment, the degree of ionization of a plasma ($\alpha$) comprises $\alpha = n+/(n+n+)$ where n is the number of neutrals, and n+ is the number of charged particles. In an embodiment, the cold plasma assembly is configured to generate a cold plasma stimulus having less than 0.1% ionized plasma.

In an embodiment, the microbiota seeding assembly is configured to deliver the one or more target species of microbiota to the biological surface responsive to one or more inputs indicative of a cold plasma stimulus delivery event.

In an embodiment, the microbiota seeding assembly is configured to deliver the one or more of wherein the microbiota seeding assembly is configured to deliver the one or more of LPS of Vf; lactic bacteria (CNCM 1-1225 gold CNCM 1-2116); skin gram positive bacterial; yeasts of the genus: *Saccharomyces, Yarrowia, Kluyveromyces,* Solarized, *Schizosaccharomyces pombe, Debaromyces, Pichia, Candida, Aspergillus* and *Penicillium,* and bacteria of the genus *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus* and *Lactobacillus* and their mixtures; the genera species: *Saccharomyces cereviseae, lipolitica Yarrowia, Kluyveromyces lactis,* Solarized, *Schizosaccharomyces pombe, Candida, Pichia, Bifidobacterium bifidum, Bifidobacterium brief, Bifidobacterium longum, Bifidobacterium animalis, Bifidobacterium lactis, Bifidobacterium infantis, Bifidobacterium adolescentis, Bifidobacterium pseudocatenulatum, Lactobacillus acidophilus, Lactobacillus alimentarius, Lactobacillus casei* subsp. *Casei, Lactobacillus casei Shirota, Lactobacillus paracasei, Lactobacillus curvatus, Lactobacillus delbruckii* subsp. *Lactis, Lactobacillus gasseri, Lactobacillus johnsonii, Lactobacillus reuteri, Lactobacillus rhamnosus, Lactobacillus sake, Lactococcus lactis, Streptococcus thermophiles, Staphylococccus carnosus* and *Staphylococcus xylosus* and their mixtures; the bacteria of the Neisseriaceae family; and bacteria grown on thermal water.

In an embodiment, a method is provided, comprising: performing a Cold Atmospheric Plasma (CAP) treatment to an external body part of a user to; and applying a pre/pro or post biotic compound to the body part of the user following the CAP treatment.

In an embodiment, a system is provided, comprising: a Cold Atmospheric Plasma (CAP) application device configured to perform a CAP treatment to an external body part of a user; and an applicator configured to apply a pre/pro or post biotic compound to the body part of the user following the CAP treatment.

DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the attendant advantages of this invention will become more readily appreciated as the same become better understood by reference to the following detailed description, when taken in conjunction with the accompanying drawings, wherein:

FIGS. 4A-4B show different strains which were evaluated using different types of CAP devices.

FIGS. 6A, 6B, and 6C shows the kINPen MED results for each strain tested.

FIGS. 7A and 7B show the PlasmaDerm results for each strain tested.

FIGS. 8A, 8B, and 8C show the Plasma One results for each strain tested.

DETAILED DESCRIPTION

Figure 1:
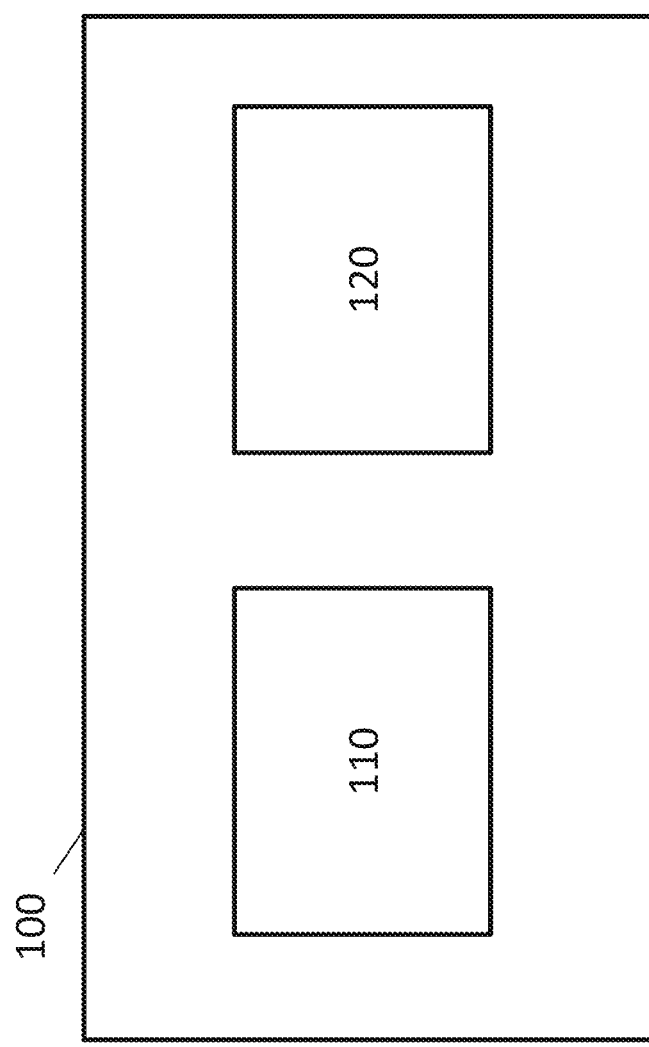
FIG. 1 shows a system that includes a Cold Atmospheric Plasma (CAP) application device and a pre/pro or post biotic compound applicator according to an embodiment.

FIG. 1 shows a system 100 that includes a Cold Atmospheric Plasma (CAP) application device 110 and a pre/pro or post biotic compound applicator 120.

Figure 2B:
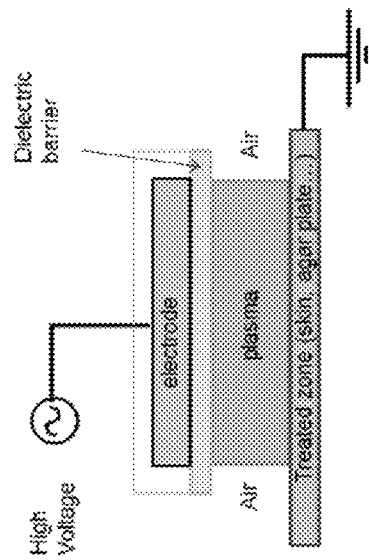
FIGS. 2A-2B show details of exemplary CAP devices according to an embodiment.
Figure 2A:
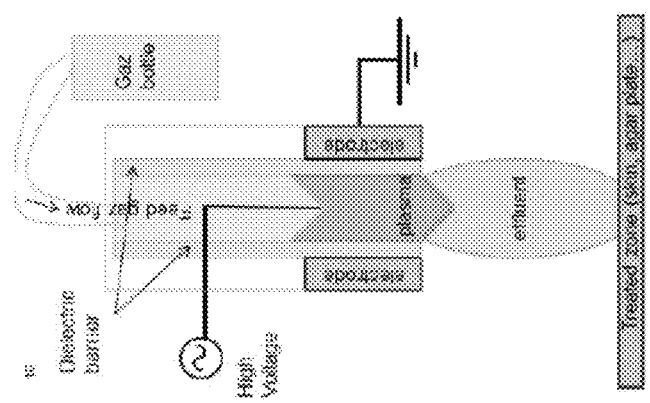

FIGS. 2A-2B show two examples of a CAP device 110, also referred to as a cold plasma assembly, in more detail. A plasma is an ionized gas composed of electrons, positively or negatively charged ionic particles, neutral atoms and molecules. Plasmas are often assimilated to the fourth state of matter, more active than solid, liquid or gas states. A plasma can be created by heating a gas or subjecting it to a strong electromagnetic field: the energy is such that it succeeds in extracting electrons from atoms. The selected devices generate a cold plasma (compatible with a use on the skin) using the Dielectric Barrier Discharge (DBD) technology at an atmospheric pressure.

In an embodiment, a Cold Atmospheric Plasma (CAP) application device 110 includes a working gas source, a plasma generator, and a controller. In an embodiment, the plasma generator applies a high voltage to a working gas source to produce a cold plasma stream.

In an embodiment, a CAP application device 110 may include a high frequency plasma generator that employs a power MOSFET in a switching amplifier circuit to produce the required radiofrequency power and drive a tuned resonator to produce a high frequency plasma discharge. See e.g. Tudoran, C. D. "HIGH FREQUENCY PORTABLE PLASMA GENERATOR UNIT FOR SURFACE TREATMENT EXPERIMENTS" Rom. Journ. Phys., Vol. 56, Supplement, P. 103-108, Bucharest, 2011 (http://www.nipne.ro/rjp/2011_56_Suppl/0103_0108.pdf). In an embodiment, a cold plasma is generated by high voltage between a stator and a rotor and is delivered through a nozzle head using a working gas.

Non-limiting examples of cold plasma technologies and methodologies include Atmospheric Pressure Discharge Plasma, Dielectric Barrier Discharge Plasma, Microwave Discharge Plasma, Pulsed Discharge Plasma, and the like. See e.g., Ruma, M. Ahasan Habib and Ranipet Hafeez Basha, A Survey of Non-thermal Plasma and their Generation Methods, International Journal of Renewable Energy and Environmental, Vol. 4, No. 1, 2016. (http://basharesearch.com/IJREEE/5040102.pdf). Further non-limiting technologies and methodologies for generating cold plasma include atmospheric pressure plasma jet, dielectric barrier discharge, direct current (DC) glow discharge, electrical discharge plasma, microwave discharge, pulsed power discharge, radiofrequency (RF) discharge, and the like.

In an embodiment, a CAP application device 110 is configured to generate a cold plasma stimulus having one or more of electrically charged particles, electrically uncharged particles, electrons, ions, and molecules, and the like. In an embodiment, a CAP application device 110 is configured to generate a cold plasma stimulus having one or more of Ultraviolet(UV) radiation, visible (VIS) radiation, Infrared (IR) radiation, and the like. In an embodiment, a CAP application device 110 is configured to generate a cold plasma stimulus having one or more of Argon, Heliox, Helium, Nitrogen, and Oxygen, and the like.

In an embodiment, a CAP application device 110 is configured to deliver to a biological surface one or more of Ultraviolet(UV) radiation, visible (VIS) radiation, Infrared (IR) radiation, free radicals, electrically charged particles, electrically uncharged particles, electrons, ions, molecules, a gas stream, and the like.

FIG. 2A shows a CAP device which is considered as a plasma "jet" or indirect plasma type of CAP device. An example of this type of device is the kINPen MED (from Neoplast Tool). The plasma is generated in the "pen" of the device from a feed gas of argon which is excited between two electrodes of the pen. The excited gas then expands into the surrounding air at the end of the capillary nozzle and appears there as plasma-jet. The type of device shown in FIG. 2A has conventionally been applied in medicine and is considered an effective treatment method in particular for infected, poor healing wounds and pathogen-induced skin diseases.

FIG. 2B shows a CAP device 110 which is based on direct dielectric barrier discharge (direct DBD) technology. An example of this type of device is the PlasmaDerm (from Cinogy). It consists on applying a voltage on an active electrode surrounded by a dielectric barrier. The treated zone (the skin or agar plate) acts as the counter-electrode of the system. The plasma is generated between the dielectric barrier and the treated zone by exciting the air present in between. The type of device shown in FIG. 2B has conventionally been used for treating chronic wound-healing disorders such as venous and arterial ulcers, pressure sores, and the diabetic foot syndrome.

While not shown there are additional type of CAP devices which may be used as CAP device 110 in the present embodiments. For instance, a CAP device may be based on the violet ray technology, which can be likened to direct DBD. An example of this type of device is the PlasmaOne (from Plasma Medical Systems). A plasma gas is generated in a glass bulb containing a rare gas. This glass bulb used as the applicator plays the role of an active electrode surrounded by a dielectric barrier (here the glass). The treated zone (the skin or agar plate) acts as the counter-electrode of the system. The plasma is generated between the glass barrier and the treated zone by exciting the air present in between.

Pre/pro or post biotic compound applicator 120, which also might be referred to as a microbiota seeding assembly, shown in FIG. 1 may be any kind of topical formulation dispenser as known in the art. Also, the compound may be applied by a hand or any instrument where appropriate In an embodiment, a microbiota seeding assembly includes one or more microbiota reservoirs. In an embodiment, a microbiota seeding assembly includes one or more detachable microbiota reservoirs. In an embodiment, a microbiota seeding assembly includes at least one replaceable cartridge including one or more reservoirs having target species of microbiota, bacteria, probiotics, microorganisms, and the like, or combinations thereof.

In an embodiment, a microbiota seeding assembly includes one or more microbiota reservoirs and at least one actuator configured to deliver a target composition (e.g., target microbiota composition, target bacteria composition, target probiotics composition, target microorganisms composition, and the like, or combinations thereof) from an interior of the reservoir to an exterior environment. For example, in an embodiment, the microbiota seeding assembly includes a plurality of reservoirs each sealed by a thin seal (e.g., a thin metal seal, an aluminum seal, a gold seal, a titanium seal, a polymeric thing film seal, and the like). In an embodiment, during operation, an electric current melts or perforates the seal causing the release a target microbiota composition within the one or more of the plurality of reservoirs to an exterior environment. In an embodiment, the microbiota seeding assembly includes one or more valves, port, flow channels, fluid flow passageways, and the like configured to assist in delivery of a target composition.

In an embodiment, the microbiota seeding assembly includes at least one reservoir having at least one release port. In an embodiment, the microbiota seeding assembly includes circuitry configured to control open and close the release ports to release a target microbiota composition within the at least on reservoir to an exterior environment. In an embodiment, the microbiota seeding assembly includes circuitry configured to control at least one of duration, flow, intensity, amount, and the like associate with the delivery of a target microbiota composition.

In an embodiment, the microbiota seeding assembly includes circuitry configured to control (electrical, electromechanical, software-implemented, firmware-implemented, or other control, or combinations thereof) at least one parameter associated with actuating delivery of a target composition (e.g., target microbiota composition, target bacteria composition, target probiotics composition, target microorganisms composition, and the like, or combinations thereof) from an interior of the reservoir; through valves, port, flow channels, fluid flow passageways and the like, to an exterior environment.

In an embodiment, the microbiota seeding assembly includes one or more environment-controlled reservoirs, compartments, containers, receptacles, cartridges, and the like. For example, in an embodiment, the microbiota seeding assembly includes one or more temperature-controlled microbiota reservoirs. In an embodiment, the microbiota seeding assembly includes at least conductive trace operable to control the temperature of a reservoirs using resistive heating. In an embodiment, the microbiota seeding assembly includes at least gas flow system to control the atmosphere of a reservoir by varying a gas composition (e.g., the gas level of one or more components, a nitrogen level, an oxygen level, and the like).

In an embodiment, the microbiota seeding assembly includes at least one of a nicrocooler, peltier nicrocooler, a peltier Thermo-Electric Cooler, a thin-film planar peltier nicrocooler, micropelt thermogenerator, operable to control the temperature of a microbiota reservoir. In an embodiment, the microbiota seeding assembly includes at least one Micro Electro Mechanical System (MEMS) microcapillary pumped loop-cooling device operable to control the temperature of a microbiota reservoir. See e.g., U.S. Pat. No. 6,976,527. In an embodiment, the microbiota seeding assembly includes one or more microfluidic components that deliver nutrients, buffer composition, solvents, and the like to microbiota with a reservoir.

Figure 3:
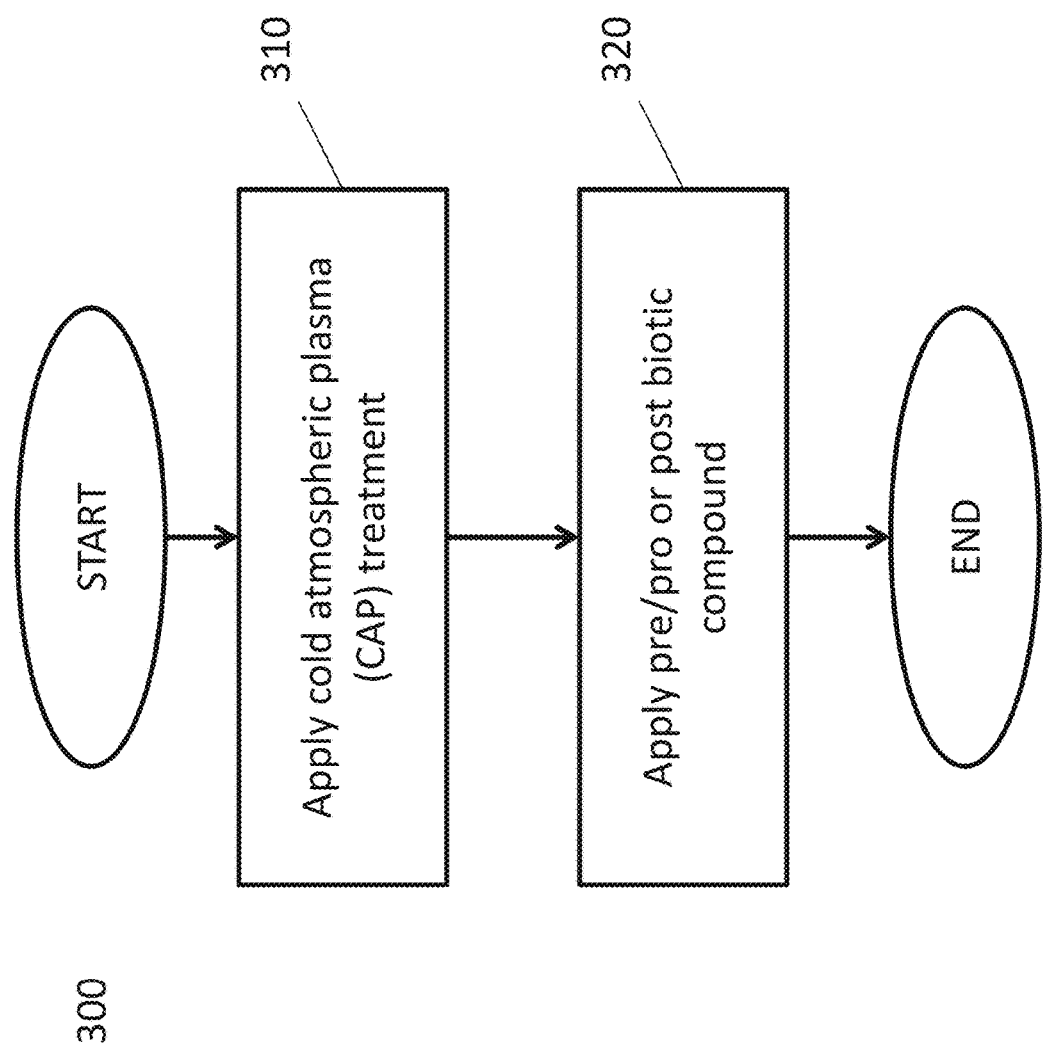
FIG. 3 shows a process for CAP treatment following application of a pre/pro or post biotic compound according to an embodiment.

FIG. 3 shows a process 300 according to an embodiment. In a first step 310, the CAP treatment is started using the device 110 as described above. In a second step 320, the pre/pro or post biotic compound is applied.

The first step 310 is aimed at eliminating certain microorganisms or bacteria. For instance, various bacterial species play a role in cosmetic problems like *Staphylococcus* species, or *Propionibacterium acnes* even yeasts like *Candida* sp. or *Malassezia* sp. FIGS. 4A and 4B provide a non-exhaustive list of strains and their respective associated disorder and culture conditions.

[Evaluation of Different CAP Devices on Strains]

Below is a description of an evaluation that was performed using the different types of CAP devices on the different strains shown in FIGS. 4A and 4B.

Three plasma devices have been tested, as described before: kINPen MED, PlasmaDerm, and Plasma One. The plasma treatments are often described in the literature as time dependent. In addition, most of the parameters of those plasma devices are frozen (as they are commercial devices). For those reasons, it was decided to vary the time as the variable parameter. For each device, we determined three values of time exposure:

Time 1: A minimum time below the recommended nominal time

Time 2: Nominal time recommended by the user guide of the device

Time 3: Maximum time allowed by the user guide of the device

Note that for the kINPen MED, a fourth intermediate value (Time 2bis: 1'30) was added in order to have a better comparison with the other devices (Table 1). Other parameters are set according to the user guide.

TABLE 1

|  | Time 1 | Time 2 | Time 2bis | Time 3 |
| --- | --- | --- | --- | --- |
| kINPen MED | 15" | 30" | 1'30" | 3' |
| PlasmaDerm | 30" | 1'30" |  | 3' |
| Plasma One | 30" | 1'30 |  | 2'30" |

The plasma generation could be impacted by the target's nature. The kINPen MED and PlasmaDerm devices were characterized by spectroscopy and electrical measurements with several kinds of targets (supports). Quite similar results were observed between a skin support and agar support and it was concluded that agar is a good substrate choice for the study. The Plasma One was not available for this characterization.

For each tested strain, the appropriate agar surface is seeded by flooding (excess liquid to ensure homogeneous distribution) with a calibrated suspension at $10^6$ $CFU^2$/ml. After 5 minutes of contact, the excess of liquid is eliminated. This seeding technique, close to the antibiogram technique on solid media, allows visualizing an homogeneous cellular mat after incubation. The antimicrobial effect of plasma is revealed by the appearance of a growth inhibition zone after incubation.

Note: Calibration of microbial suspensions at $10^6$ $CFU^2$/ml was validated during pre-tests to ensure a homogeneous microbial mat. The agar plates used for the evaluation of the PlasmaDerm device are poured into large Petri dishes in order to adapt the substrate to the dimensions of the applicator.

Specific criteria were established for this evaluation:
No effect (no inhibition zone)
Low effect (some inhibition zones)
Average effect (treated zone partially inhibited)
Strong effect (inhibition zone≥to the dimensions of the applicator)

Figure 5A:
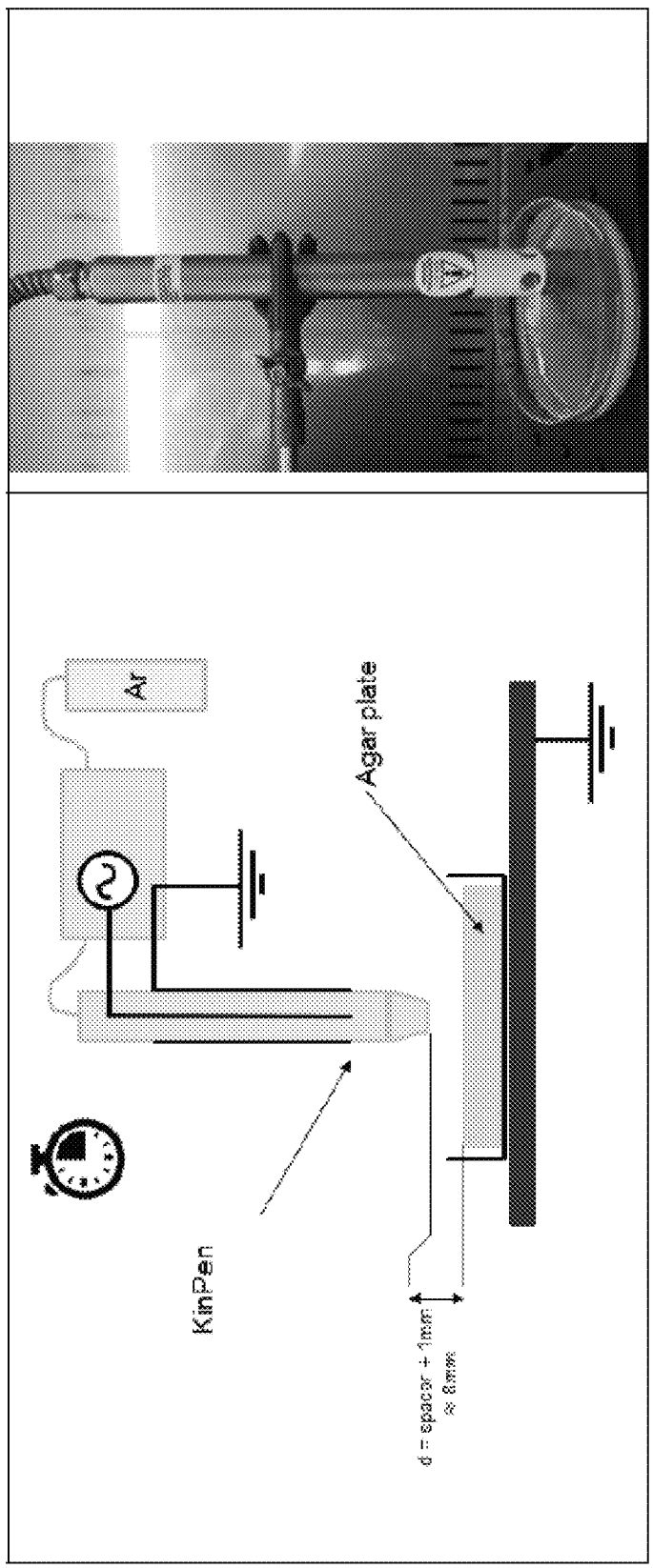
FIG. 5A shows a configuration of the kINPen MED CAP device used in an evaluation.

Following these criteria, the strains can be classified from the more sensitive tested strain (Rank 1) to the less sensitive tested strain (Rank 16).

kINPen MED:

As shown in FIG. 5A, the distance between the nozzle and the agar plate has been fixed at the distance of the spacer+1 mm, as recommended by the user guide. The treatment is static for technical convenience. The feed gas used is Argon at a gas flow of 5 l/min. Two tests per time exposure (n=2) was performed for this device.

Figure 5B:
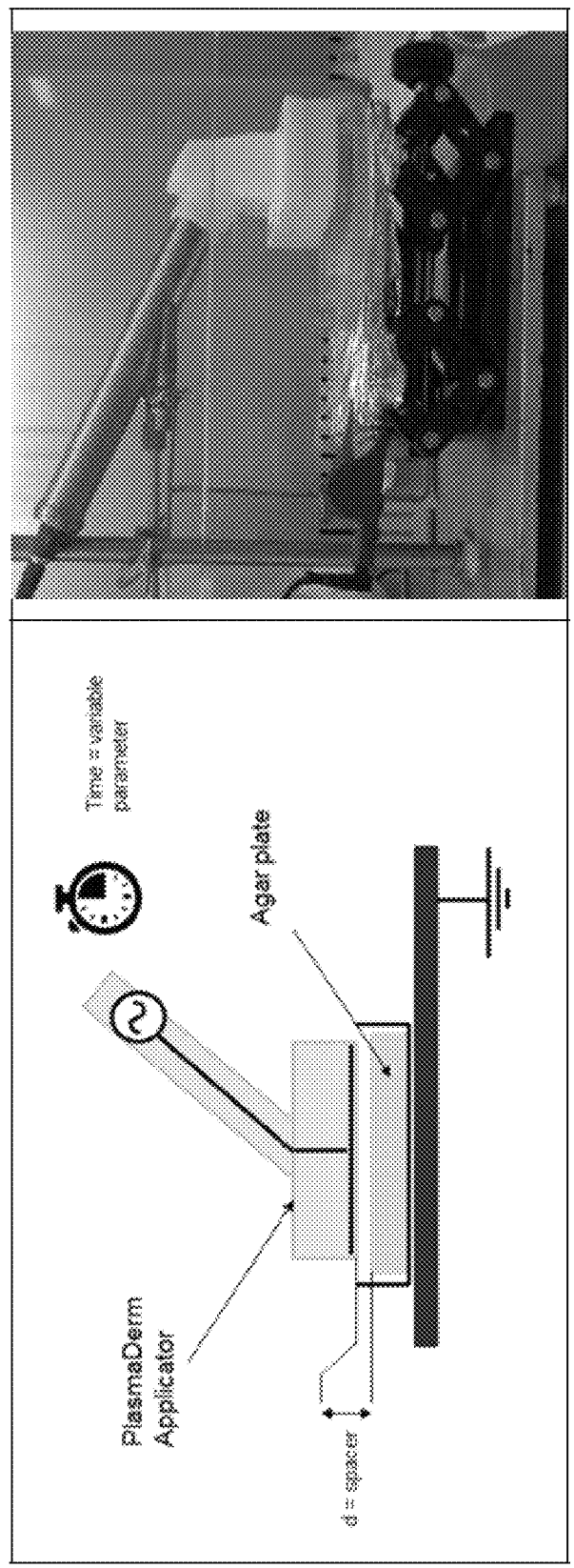
FIG. 5B shows a configuration of the PlasmaDerm CAP device used in an evaluation.

PlasmaDerm:

As shown in FIG. 5B, the distance from the applicator is determined by the spacers of the applicator. The applicator is specifically designed for an application on the skin. In order to adapt the use of the applicator on an agar plate (instead of the skin), we proceeded with a modification of the applicator:

The majority of spacer cones have been cut in order to enlarge the surface of plasma in contact with agar plate The electrode has been stiffened by an outer plastic plate The agar plate is laid on a grounded conductive metal plate in order to allow a good generation of plasma. Only one test per time exposure (n=1) was performed for this device (technical and organizational constraints).

Figure 5C:
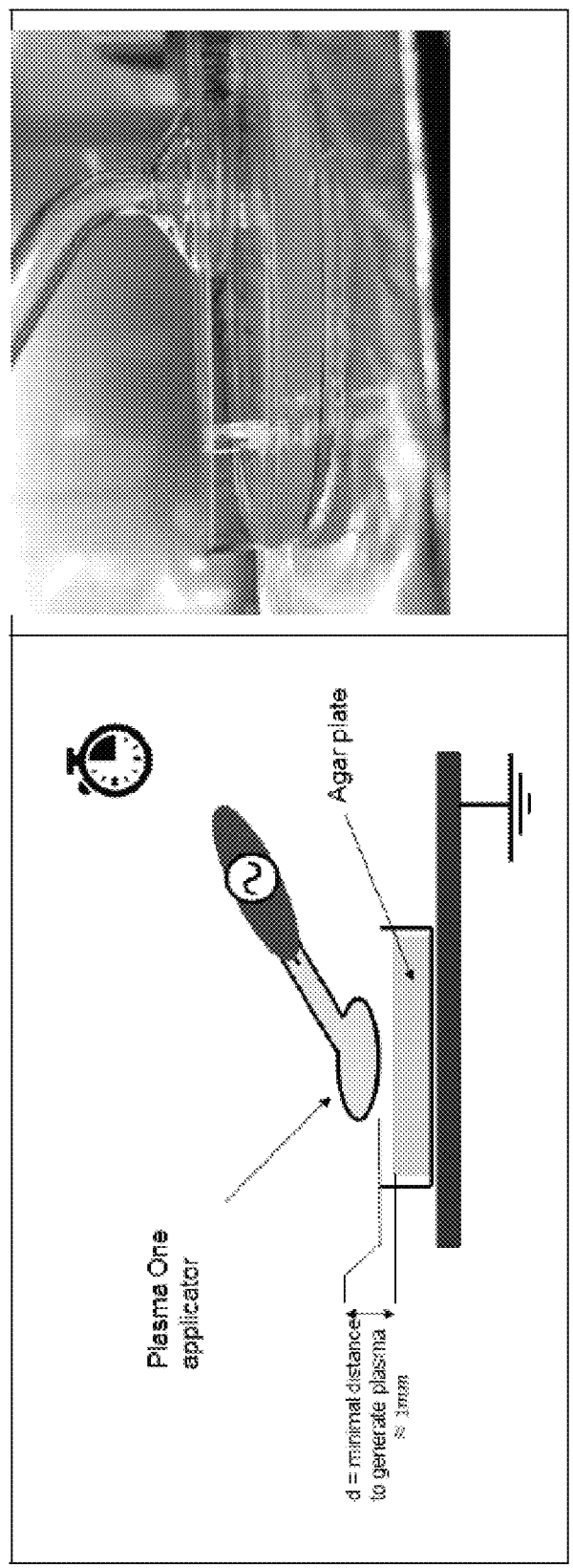
FIG. 5C shows a configuration of the Plasma One CAP device used in an evaluation.

Plasma One:

As shown in FIG. 5C, the distance set between the applicator an agar is the minimum distance to generate the plasma without contact with the agar. It is about 1 mm, as recommended by the user guide of the device. The agar plate is laid on a grounded conductive metal plate in order to allow a good generation of plasma. Two tests per time exposure (n=2) was performed for this device.

[Evaluation Results]

kINPen MED

FIGS. 6A-6C shows the kINPen MED results for each strain tested, efficacy and ranking (results shown here are representative of two independent experiments).

For all evaluated species, the kINPen MED device has an antimicrobial effect with at least one inhibition area for a time exposure. Moreover, it has been clearly observed for this device that the diameter of the inhibition area increases as a function of the exposure time. With the exception of *Malassezia furfur*, for which the inhibition area only appears after 3 minutes of treatment, all strains are inhibited by 15 seconds treatment.

PlasmaDerm:

FIGS. 7A-7B show the PlasmaDerm results for each strain tested. PlasmaDerm has strong antimicrobial efficacy on two species, *Propionibacterium acnes* (collection and wild) and *Candida albicans*. For the other tested strains, the inhibition areas are partial with different levels of efficacy from no efficacy (*Malassezia furur*) to average efficacy from 1 min 30 s (*Staphylococcus epidermidis* collection) according to the strains. A large variability is observed in the results. One possible root cause could be an applicator issue, in spite of the modifications applied on it. A better material set up with an applicator dedicated for application on agar may lead to better results. From the point of view of the cosmetic problems targeted by the choice of strains, this device seems better positioned for an anti-acne (*Propionibacterium acnes*) and axillary odor (*Corynebacterium xerosis* and *Corynebacterium jeikeium*) application.

Figure 8A:
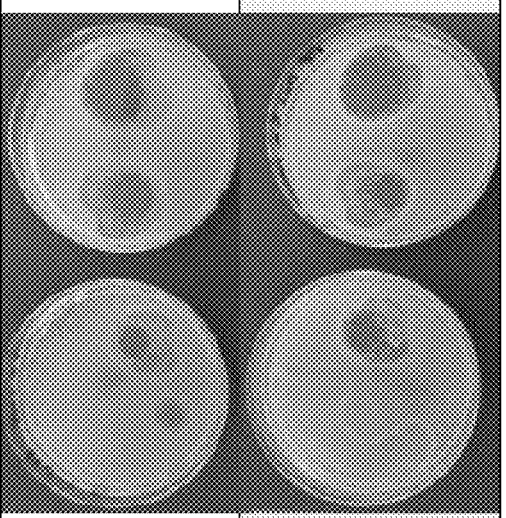

Plasma One:

FIGS. 8A-8C show the Plasma One results for each strain tested. The plasma generated by Plasma One induces significant inhibition area within 30 seconds of exposure and for all the strains tested. Antimicrobial efficacy is strong for 14 of the 16 strains and average for the two remaining strains. Plasma One's broad spectrum of action makes this device an interesting tool for all the cosmetic issues targeted in this vitro test. During the use of Plasma One on skin, no excessive or unpleasant heating sensation was observed to be felt.

[Evaluation Observations]

Under the test conditions, the three plasma sources tested showed antimicrobial properties with levels of efficacy that are dependent on the strains. The potential of PlasmaDerm is highlighted in the acne and deodorant disorders as well as the potential of the kINPen MED for the problems of atopy and acne. Plasma One, by its broad spectrum of action, appears to be interesting in all the cosmetic problems targeted by the choice of strains. The impact of the temperature on the observed antimicrobial activities of the kINPen MED remains to be determined. Tests with the kINPen MED with a dynamic application, as recommended by the user guide, could be done in order to ensure that the antimicrobial effect is due to plasma rather than temperature. Indeed, a dynamic treatment avoids an agar heating during the treatment. Our results on *Pseudomonas aeruginosa* and *Candida albicans* confirm the efficacy of Cold Atmospheric Plasma on these germs as described in the literature (Atmospheric pressure no thermal plasmas for bacterial biofilm prevention and eradication, Svetlana A. Ermolaeva, 2015). The next plasma studies will be oriented towards multi strains culture tests on skin reconstructs, targeting acne and atopy applications.

Therefore, based on the above, step 310 may vary based the type of CAP device and the strain which is targeted.

In step 320, the applicator 120 may be the microbiota seeding assembly structure as described above, but it is not limited to this structure.

The type of compound to be applied to the skin or scalp of the user will vary based the target treatment. Below is a list of compound elements and factors which the inventors have considered.

Thermal Waters
  Examples: Vichy, La Roche-Posay, St Gervais and competitors

Sources of Carbon
  Simple or complex sugars and their homo or hetero polymers of the following compounds: Adonitol; Amygdaloside; Arabinose; Cellobiose; Dulcitol; Erythritol; Esculine; Fructose; Galactose; Glucose; Glycerol; Glycogen; Inositol; Inulin; Lactose; Maltose; Mannitol; Mannose; Melezitose; Melibiose; Raffinose; Rhamnose; Ribose; Salicin; Sorbitol; Sorbose; Starch (starch); Sucrose (sucrose); Trehalose; Xylose, as well as their derivatives phosphatic, sulfated, or substituted as the proxylane with xylose
  Di, tri, and polysaccharides
  Glycogen, glucose polymer and all polymers of the latter
  Hetero saccharides
  and C glycosides
  Honey, maple syrup and other natural complex sugars
  The poly hydroxy butyrate and its monomer
  Acid formic, acetic, propionic and including lactic acid and those of Glycolysis and the cycle of Krebs and all fat until C18, saturated or unsaturated acids. Their glycerin derivatives and derived cellulose
  Traditional genres *Bifidobacterium* spp. and the *Lactobacillus* spp. and their hydrolysates
  The whole of bacteria constituting the natural skin flora such as for example the family Xanthomonadaceae
  Extracts plant, rich in carbohydrates and their polymers
  Particulate air pollution Nitrogenous Sources
  All derivatives of ammonium and nitrate/nitrite
  Hydrogenated compounds such as: 1 are ions ammonium $NH_4^+$, the ions reagent $NH_2^-$,$_2$ NHR primary amines and secondary $R_2NH$, $HN_3$, hydrazine N azothydrique $acid_2H_4$
  The compounds oxygenated: the nitrosyle $N_4O$ azide; nitrous nitrogen $N_2O$, the nitrogen monoxide NO, $N_2O_3$, nitrogen dioxide $NO_2$, its Dimer tetraoxyde of nitrogen $N_2O_4$, vanadium nitrogen $N_2O_5$ and the nitrogen trioxide $No._3$
  The nitrogen oxoanions: ion nitrate $NO_3^-$ and nitrite $NO_2^-$
  all of the amino acids including taurine and their peptide polymer, hetero or homo
  The bacteria contained in thermal, mineral and drinking waters or sea of oligotrophic or eutrophic biotopes
  Yeasts, the peptones what whatever their origin and treatments
  Algae (macro and micro) and plant extracts
  Urea, the indole and its derivatives Trace Elements and Macroelements
  Calcium, phosphorus, Potassium, sulphur, Sodium, chlorine and Magnesium.
  All mineral derivatives (salts) and organic carbon oxygen and nitrogen such as $CaCl_2$, $MgSO_4$, NaCl, $MnSO_4$, phosphates . . . + carbohydrates
  Trace elements: Ti, V, Cr, Mn, Fe, Co, Ni, Cu, Zn, As, Se, Br, Mo, Ag, to, Cd, Sn, I, Li, Cl, Hg, Pb, yttrium, and salts of lanthanon; as sulfates, nitrates and phosphates or chloride salts Vitamins and Derivatives
  Vitamin K, B8 and B12, Thiamine riboflavin, Nicotinamide, Pantothenic acid, Pyridoxine and derivatives, biotin, folic acid, cyanocobalamin and Ascorbic acid
  Carotenoids and their derivatives, retinol and its derivatives, calcitriol, tocopherols, tocotrienols, the phylloquinone, the menaquinone (Vit K2) and Co Enzyme Q8 and Q10.
  carnitine, orotic acid para amino benzoique acid and its derivatives, acid Brewers, dimethylglycine and Laetrile (amygdalin).

Probiotics, Bacterial Immunoregulatory and Lysates of These
  LPS of Vf
  lactic bacteria (CNCM 1-1225 gold CNCM 1-2116)
  skin Gram positive bacteria
  yeasts of the genus *Saccharomyces, Yarrowia, Kluyveromyces,* Solarized, *Schizosaccharomyces pombe, Debaromyces, Pichia, Candida, Aspergillus* and *Penicillium*, and bacteria of the genus *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus* and *Lactobacillus* and their mixtures
  more particularly the following of these genera species: *Saccharomyces cereviseae, lipolitica Yarrowia, Kluyveromyces lactis,* Solarized, *Schizosaccharomyces pombe, Candida, Pichia, Bifidobacterium bifidum, Bifidobacterium brief, Bifidobacterium longum, Bifidobacterium animalis, Bifidobacterium lactis, Bifidobacterium infantis, Bifidobacterium adolescentis,*

*Bifidobacterium pseudocatenulatum, Lactobacillus acidophilus, Lactobacillus alimentarius, Lactobacillus casei* subsp. *Casei, Lactobacillus casei Shirota, Lactobacillus paracasei, Lactobacillus curvatus, Lactobacillus delbruckii* subsp. *Lactis, Lactobacillus gasseri, Lactobacillus johnsonii, Lactobacillus reuteri, Lactobacillus rhamnosus, Lactobacillus sake, Lactococcus lactis, Streptococcus thermophiles, Staphylococccus carnosus* and *Staphylococcus xylosus* and their mixtures Specifically, *Lactobacillus johnsonii* (CNCM 1-1225), *Lactobacillus paracasei* (CNCM 1-2116), *Bifidobacterium adolescentis* (CNCM 1-2168), *Bifidobacterium longum* (CNCM 1-2170), *Bifidobacterium lactis* (CNCM 1-3446), *Bifidobacterium longum* (BB536), and their mixtures.

The bacteria of the Neisseriaceae family

Bacteria grown on thermal water (La Roche-Posay (cf 79203), Saint Gervais or Vichy)

Physical Factors to Consider Factors pH, temperature, salinity, $a_w$ (activity of water (free water) affected by salinity, sugars, moisture absorbers, urea, glycerol), or oxygenation of the skin. We know that *S. aureus* is able to grow if $a_w$ is >0.83, and that *S. epidermidis* is able to grow if aw is >0.87. If we control an aw at 0.85 then only *S. aureus* is able to grow, but if we increase the aw over 0.87, then *S. epidermidis* will compete with *S. aureus*. In the same way of thinking, anaerobic bacteria like *P. acnes* take advantage for growing with a gaseous environment without oxygen.

While the above method is described as being performed on a system that includes two separate devices, a single device may be used which incorporates the structural features of each of the devices 110 and 120. Additionally, each device in the system 100 may be connected to an external computer, processing circuitry, device, or network.

In an example, a communication interface (I/F) may be provided within the system which can include circuitry and hardware for communication with a client device (such as an external computer or mobile device). The communication interface may include a network controller such as BCM43342 Wi-Fi, Frequency Modulation, and Bluetooth combo chip from Broadcom, for interfacing with a network. The hardware can be designed for reduced size. For example, the processor may be a CPU as understood in the art. For example, the processor may be an APL0778 from Apple Inc., or may be other processor types that would be recognized by one of ordinary skill in the art. Alternatively, the CPU may be implemented on an FPGA, ASIC, PLD or using discrete logic circuits, as one of ordinary skill in the art would recognize. Further, the CPU may be implemented as multiple processors cooperatively working in parallel to perform the instructions of the inventive processes described above. The client device may also have similar circuitry and hardware as described above.

In an embodiment, the system may include a user interface, which may be in the form of input buttons on the housing of the system (or each device), or it may be in the form of a contact-sensitive display, such as a capacitive or resistive touch screen display.

In an embodiment, the system may include a memory that stores software for controlling the styling tool, or for storing user data or other information.

In an embodiment, the operating system of the external client device can have a user interface that is configured to perform multiple functions. In an aspect, the client device can be in communication with a network and enable the user interface access to the Internet as well as Internet of Things (IOT). As can be appreciated, the network can be a public network, such as the Internet, or a private network such as an LAN or WAN network, or any combination thereof and can also include PSTN or ISDN sub-networks. The network can also be wired, such as an Ethernet network, or can be wireless such as a cellular network including EDGE, 3G and 4G wireless cellular systems. The wireless network can also be WiFi, Bluetooth, or any other wireless form of communication that is known. In an example, the network can access a server hosting media, protocols, products, personal accounts, stored usage data, and other data related to the system.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

What is claimed is:

1. A skin microbiota modulation device, comprising:
a cold plasma assembly configured to
generate a cold plasma stimulus including a partially ionized gas mixture, and
interrogate a biological surface having resident bacteria thereon with the cold plasma stimulus, the cold plasma stimulus being generated to eliminate the resident bacteria on the biological surface; and
a bacteria seeding assembly including at least one replaceable cartridge including one or more reservoirs including one or more target species of bacteria, each reservoir of the one or more reservoirs being temperature-controlled, the bacteria seeding assembly configured to deliver the one or more target species of bacteria to the biological surface.

2. The skin microbiota modulation device of claim 1, wherein the cold plasma assembly is configured to generate a cold plasma stimulus having one or more of electrically charged particles, electrically uncharged particles, electrons, ions, and molecules.

3. The skin microbiota modulation device of claim 1, wherein the cold plasma assembly is configured to generate a cold plasma stimulus having one or more of Argon, Heliox, Helium, Nitrogen, and Oxygen.

4. The skin microbiota modulation device of claim 1, wherein the cold plasma assembly includes at least one of an atmospheric pressure plasma jet, a dielectric barrier discharge plasma actuator, a gliding arc device, a piezoelectric direct discharge plasma device, a plasma actuator, a plasma needle, and a plasma pencil.

5. The skin microbiota modulation device of claim 1, wherein the cold plasma assembly is configured to generate a cold plasma stimulus of a character and for a duration sufficient to modulate the activity of skin microbiota on the biological surface.

6. The skin microbiota modulation device of claim 1, wherein the cold plasma assembly is configured to generate a cold plasma stimulus that is less than 60° Celsius at the point of application.

7. The skin microbiota modulation device of claim 1, wherein the cold plasma assembly is configured to generate a cold plasma stimulus that is less than 40° Celsius at the point of application.

8. The skin microbiota modulation device of claim 1, wherein the cold plasma assembly is configured to generate a cold plasma stimulus having less than 0.1% ionized plasma.

9. The skin microbiota modulation device of claim 1, wherein the bacteria seeding assembly is configured to deliver the one or more target species of bacteria to the biological surface responsive to one or more inputs that the cold plasma stimulus interrogation to the biological surface has completed.

10. The skin microbiota modulation device of claim 1, wherein the bacteria seeding assembly is configured to deliver the one or more of LPS of Vf; lactic bacteria (CNCM I-1225 gold CNCM 1-2116); skin gram positive bacterial; yeasts of the genus: *Saccharomyces, Yarrowia, Kluyveromyces*, Solarized, *Schizosaccharomyces pombe*, Debaromyces, *Pichia, Candida, Aspergillus* and *Penicillium*, and bacteria of the genus *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus*, Oenococcus and *Lactobacillus* and their mixtures; the genera species: *Saccharomyces* cereviseae, *lipolitica Yarrowia, Kluyveromyces lactis*, Solarized, *Schizosaccharomyces pombe, Candida, Pichia, Bifidobacterium bifidum, Bifidobacterium brief, Bifidobacterium longum, Bifidobacterium animalis, Bifidobacterium lactis, Bifidobacterium infantis, Bifidobacterium adolescentis, Bifidobacterium pseudocatenulatum, Lactobacillus acidophilus, Lactobacillus alimentarius, Lactobacillus casei* subsp., *Casei, Lactobacillus casei* Shirota, *Lactobacillus paracasei, Lactobacillus curvatus, Lactobacillus* delbruckii subsp., *Lactis, Lactobacillus* gasseri, *Lactobacillus johnsonii, Lactobacillus reuteri, Lactobacillus rhamnosus, Lactobacillus sake, Lactococcus lactis, Streptococcus* thermophiles, *Staphylococccus carnosus* and *Staphylococcus* xylosus and their mixtures; the bacteria of the Neisseriaceae family; and bacteria grown on thermal water.

11. The skin microbiota modulation device of claim 1, wherein the temperature of said each reservoir of the one or more reservoirs is controlled via at least one of a nicrocooler, a peltier nicrocooler, a peltier thermos-electric cooler, a thin-film planar peltier cooler, and a micropelt thermogenerator.

12. The skin microbiota modulation device of claim 1, wherein the temperature of said each reservoir of the one or more reservoirs is controlled via a conductive trace using resistive heating.

13. The skin microbiota modulation device of claim 12, wherein said each reservoir of the one or more reservoirs includes a seal in contact with the conductive trace and the conductive trace is configured to perforate the seal and release the one or more target species of bacteria from the respective reservoir.

14. The skin microbiota modulation device of claim 1, wherein the bacteria seeding assembly includes a gas flow system configured to control the atmosphere of said each reservoir of the one or more reservoirs via varying a gas composition.

15. The skin microbiota modulation device of claim 1, wherein the bacteria seeding assembly includes a microfluidic channel network fluidly coupled to said each reservoir of the one or more reservoirs and the microfluidic channel network is configured to deliver a fluid to said each reservoir of the one or more reservoirs.

16. The skin microbiota modulation device of claim 15, wherein the fluid is at least one of a nutrient solution, a buffer composition, and a solvent.

17. A method, comprising:
performing a Cold Atmospheric Plasma (CAP) treatment to an external body part of a user having a resident bacteria thereon, the CAP treatment eliminating the resident bacteria from the body part; and
applying a pre/pro or post biotic compound to the body part of the user following the CAP treatment via a bacteria seeding assembly including at least one replaceable cartridge including one or more reservoirs including one or more target species of bacteria, each reservoir of the one or more reservoirs being temperature-controlled, the bacteria seeding assembly configured to deliver the one or more target species of bacteria to the external body part of a user.

18. A system, comprising:
a Cold Atmospheric Plasma (CAP) application device configured to perform a CAP treatment to an external body part of a user having resident bacteria thereon to eliminate the resident bacteria, the CAP application device including a bacteria seeding assembly including at least one replaceable cartridge including one or more reservoirs including one or more target species of bacteria, each reservoir of the one or more reservoirs being temperature-controlled, the bacteria seeding assembly configured to deliver the one or more target species of bacteria to the biological surface; and
an applicator configured to apply a pre/pro or post biotic compound to the body part of the user following the CAP treatment.

* * * * *

UNITED STATES PATENT AND TRADEMARK OFFICE
CERTIFICATE OF CORRECTION

PATENT NO. : 11,229,806 B2
APPLICATION NO. : 15/973931
DATED : January 25, 2022
INVENTOR(S) : Barbarat et al.

It is certified that error appears in the above-identified patent and that said Letters Patent is hereby corrected as shown below:

On the Title Page

Column 2, Item (57), under "ABSTRACT", Line 6, delete "micobiota," and insert -- microbiota, --, therefore.

Column 2, Item (57), under "ABSTRACT", Line 8, delete "micobiota" and insert -- microbiota --, therefore.

In the Claims

In Column 13, Claim 10, Line 23, delete "Peptostrepococcus," and insert -- Peptostreptococcus, --, therefore.

In Column 13, Claim 10, Line 26, delete "cereviseae, lipolitica" and insert -- cerevisiae, lipolytica --, therefore.

In Column 13, Claim 10, Line 35, delete "delbruckii" and insert -- delbrueckii --, therefore.

In Column 13, Claim 10, Lines 38-39, delete "Staphylococccus" and insert -- Staphylococcus --, therefore.

Signed and Sealed this
Thirty-first Day of May, 2022

Katherine Kelly Vidal
*Director of the United States Patent and Trademark Office*